United States Patent
Kim et al.

(10) Patent No.: US 9,827,201 B2
(45) Date of Patent: Nov. 28, 2017

(54) NATURAL LUBRICANT FOR DIRECT COMPRESSION AND METHOD FOR PREPARING NATURAL TABLET USING THE SAME

(71) Applicant: CJ Cheiljedang Corporation, Seoul (KR)

(72) Inventors: Sung Ki Kim, Gyeonggi-do (KR); Jae Seok Shim, Gyeonggi-do (KR); Sang Hyeon Kim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 13/871,529

(22) Filed: Apr. 26, 2013

(65) Prior Publication Data

US 2013/0296445 A1    Nov. 7, 2013

(30) Foreign Application Priority Data

May 3, 2012    (KR) .................. 10-2012-0046731

(51) Int. Cl.
*A01N 25/00* (2006.01)
*A61K 47/00* (2006.01)
*A23L 1/20* (2006.01)
*A61K 9/20* (2006.01)

(52) U.S. Cl.
CPC .................. *A61K 9/2068* (2013.01)

(58) Field of Classification Search
None
See application file for complete search history.

(56) References Cited

U.S. PATENT DOCUMENTS

2005/0037025 A1*    2/2005    Gow et al. ............... 424/195.18

FOREIGN PATENT DOCUMENTS

| JP | 04124124 A | * | 4/1992 |
| JP | H05-004914 A | | 1/1993 |
| JP | 2001-039863 A | | 2/2001 |
| JP | 2007-320856 A | | 12/2007 |
| KR | 10-2008-0090101 A | | 10/2008 |

OTHER PUBLICATIONS

Merissa (Making and Using Bean Flour, Published Jan. 4, 2012, http://www.littlehouseliving.com/making-and-using-bean-flour.html).*
Mung Bean Flour (http://www.cooksinfo.com/mung-bean-flour; retrieved from the internet Jun. 30, 2015).*
Yamahara et al. in JP04124124A; published Apr. 24, 1992; English abstract).*
Yamahara et al. (JPH04124124A; published Apr. 24, 1992; Full English translation).*
What is Calcium Carbonate (Industrial Minerals Association North America, http://www.ima-na.org/page/what_is_calcium_carb, retrieved from the internet Nov. 16, 2016).*
International Search Report and Written Opinion dated in PCT/KR2013/003640 Aug. 29, 2013.

* cited by examiner

*Primary Examiner* — Dennis Heyer
*Assistant Examiner* — Daniel M Podgorski
(74) *Attorney, Agent, or Firm* — Swanson & Bratschun, L.L.C.

(57) ABSTRACT

The present invention relates to a natural lubricant for direct compression and a method of preparing a synthetic additive-free natural tablet using the same. More particularly, the invention provides a crude fat-containing bean powder, which is used as a natural lubricant, and a method of preparing a natural tablet using the bean powder by a dry granulation process which is carried out using a roller compactor.

8 Claims, No Drawings

NATURAL LUBRICANT FOR DIRECT COMPRESSION AND METHOD FOR PREPARING NATURAL TABLET USING THE SAME

CROSS-REFERENCE(S) TO RELATED APPLICATIONS

The present invention claims priority of Korean Patent Application No. 10-2012-0046731, filed on May 3, 2012, which is incorporated herein by reference.

TECHNICAL FIELD

The present invention relates to a natural lubricant for direct compression and a method for preparing a synthetic additive-free natural tablet using the same.

BACKGROUND ART

In recent years, as consumer interest in Well-being and natural foods has increased, the use of natural additives in place of synthetic additives in the food industry has gradually increased, and the range of application thereof also has continued to increase.

In particular, in pharmaceutical drugs and health functional foods, safety and environmentally friendly factors in production processes are considered important, and thus many products containing natural components are being developed and the market size thereof is also increasing.

In the pharmaceutical and food industries, various excipients are used to prepare internal solid dosage forms. These excipients are widely involved in the flow properties of mixtures, compression properties in tablet preparation, disintegration properties for smooth disintegration, sticking properties in which powder sticks to the surface of tablet compression punches to cause defects on the tablet surface, capping in which the upper portion of tablets is peeled off in a cap shape during compression, lamination in which a tablet is peeled off in a layered fashion, and binding properties for enhancing the hardness of tablets.

Generally, pharmaceutical drug products are mostly produced by a wet granulation process in which a solution is added to powders for granulation. In the wet granulation process, when granules are over-dried, a large amount of fine powder occurs during the tableting of the over-dried granules and this fine powder has poor flowability in a tablet compression machine, and thus causes a variation in the weight of tablets and results in capping and lamination. For this reason, non-natural synthetic additives such as a binder (hydroxypropylmethylcellulose, corn starch etc.) are used for the granulation of such powder.

If active ingredients are sensitive to water or heat, dry granulation processes are sometimes used, and a roller compactor is widely used as one of dry granulation processes which are generally used. Most of the dry granulation processes do not use moisture, and thus do not cause problems of picking and sticking in which uneven spots occur on the surface of tablets.

Direct compression is a method of making complete tablets by mixing each components and compressing the mixture into tablets without changing any component.

Despite many efforts to substitute natural additives for synthetic additives, synthetic additives are inevitably being used in tablet products, which are widely used in the pharmaceutical and health functional food industries, due to various problems occurring during processes, including sticking which a disc (a plate with which a mixture for compression comes into contact) sticks to a surface of punch in a tablet compression machine.

Among these synthetic additives, stearic acid or magnesium stearate which is most widely used as a lubricant shows excellent lubricant performance even when it is used in an amount of 0.5-1 wt % based on the total weight of a mixture for compression, and also assists in improving the flowability of the mixture. Also, if the flowability of a pharmacological mixture needs to be improved, a glidant such as silicon dioxide or talc is widely used. However, the above materials are all chemical synthetic products which significantly interfere with the development of formulations comprising only natural components.

DISCLOSURE

Technical Problem

The present inventors have conducted extensive studies to overcome the above-described problems, and as a result, could develop a natural tablet comprising only natural component by using crude fat-containing bean powder as a natural lubricant in place of the synthetic additive magnesium stearate, which has been most frequently used as a lubricant, to prevent a sticking phenomenon from occurring in direct compression, and ensuring flowability by a dry granulation process using a roller compactor.

Therefore, it is an object of the present invention to provide crude fat-containing bean powder as a natural lubricant substituting for a synthetic additive.

Another object of the present invention is to provide a method of preparing a natural tablet using the natural lubricant by only a physical method.

Technical Solution

The present invention provides bean powder having a crude fat content of 10-25% as a natural lubricant substituting for a synthetic additive.

The present invention also provides a method of preparing a natural tablet by a dry granulation process using a roller compactor, to prepare a natural tablet using the natural lubricant by only a physical method.

Advantageous Effects

The present invention provides a natural lubricant which can be used in direct compression after the mixing of an active ingredient and excipients, unlike a synthetic lubricant which is generally added before tablet compression in the pharmaceutical and food industries. This natural lubricant can prevent a sticking phenomenon from occurring in direct compression. In addition, according to the present invention, the flowability of a mixture for direct compression can be improved by a dry granulation process using a roller compactor, and a natural tablet having ensured productivity can be provided.

Best Mode

As used herein, the term "natural lubricant" is a material having a lubricant effect, which is prepared by a physical process without carrying out a chemical extraction process or a chemical reaction. In the present invention, pharmaceutically acceptable lubricants, for example, including, but not limited to, magnesium stearate, polyethylene glycol, talc, calcium stearate, microcrystalline cellulose, etc., are defined as chemical synthetic products (hereinafter referred to as synthetic lubricants), and the inventive natural lubricant material substituting for such synthetic lubricants is defined as a natural lubricant.

As used herein, the term "natural tablet" means a tablet prepared from pharmacologically useful raw materials by only a physical compression process without carrying out a chemical extraction process or a chemical reaction.

The present invention provides crude fat-containing bean powder as a natural lubricant substituting for magnesium stearate which has been mainly used as a lubricant.

The bean powder is a product obtained by powdering beans and preferably has a crude fat content of 10-25%. Examples of the bean powder include white bean powder, black bean powder, roasted white bean powder, and roasted black bean powder. Preferably, white bean powder may be used.

The use of the crude fat-containing bean powder imparts lubricant properties without needing to use a conventional synthetic lubricant, and this appears to be because of the crude fat component of the bean powder. The bean powder can be used not only in the preparation of granules for preparing tablets, but also a natural lubricant before and after tablet compression.

The present invention also provides a method of preparing a natural tablet by a dry granulation process using a roller compactor, to prepare the tablet using the natural lubricant by only a physical method.

More specifically, the present invention provides a method for preparing a natural tablet, the method comprising the steps of:

a) mixing an active ingredient, a binder, an excipient and a disintegrant to prepare mixed powder;

b) adding to and mixing with the mixed powder the natural lubricant; and c) compacting the mixed powder using a roller compactor so as to form a sheet and granulating the sheet.

Fundamentally, the following components may be used in the preparation of the natural tablet:

(a) active ingredient;
(b) binder;
(c) excipient;
(d) disintegrant; and
(e) (natural) lubricant.

The active ingredient that is used in the preparation of the tablet is not specifically limited, and examples thereof include various types of natural extracts.

Examples of a pharmaceutically acceptable binder include starch, modified starch, microcrystalline cellulose, cellulose and its derivatives, sucrose, gelatin, etc. Preferably, a binder prepared by a physical process, for example, starch, starch paste, natural gum (gum Ghatti or guar gum) or a natural calcium material, may be used in the present invention.

The content of the binder in the natural tablet may be about 0-60 wt %, and preferably 30-60 wt %, based on the total weight of the natural tablet.

Examples of a pharmaceutically acceptable excipient include lactose, glucose, sucrose, cellulose, crystalline cellulose, milk calcium, etc. Preferably, an excipient prepared by a physical process, for example, starch or a natural calcium material, may be used in the present invention.

The content of the excipient in the natural tablet may be about 0-60 wt %, and preferably 30-50 wt % based on the total weight of the natural tablet.

Examples of a pharmaceutically acceptable disintegrant include starch, cellulose, a crosslinked polymer such as polyvinyl pyrrolidone and alginic acid. Preferably, a disintegrant prepared by physical process, for example, starch or a natural calcium material, may be used in the present invention.

The content of the disintegrant in the natural tablet may be about 0-5 wt % based on the total weight of the natural tablet.

In a preferred embodiment of the present invention, a natural calcium material serving as a binder for increasing the binding strength of a mixture for natural tablet preparation, an excipient for increasing the amount of the mixture, and a disintegrant for improving the disintegrant property of the mixture is used to prepare the natural tablet.

The natural calcium material that is used in the present invention is a natural excipient which also serves as a binder and a disintegrant, and functions to improve the water absorbing property of an active ingredient and to hold the oil and fat components of the crude fat-containing soybean powder which is added as the natural lubricant. Thus, it also functions to help the natural lubricant to most reproducibly exhibit a lubricant property.

The natural calcium material as a binder may be seaweed calcium powder, shell calcium powder, eggshell calcium powder or the like.

In the present invention, the crude fat-containing bean powder as a natural lubricant may be present in an amount of about 0.1-10 wt %, and preferably 2-6 wt %, based on the total weight of the natural tablet.

In a preferred embodiment of the present invention, a synthetic lubricant which is usually added before tablet compression is not used, and the natural lubricant is added to and mixed with a mixture of an active ingredient and an excipient.

In step a) of the method of the present invention, the mixing time is not specifically limited, but is preferably 5-40 minutes, and 10-30 minutes, depending on the composition of the mixture.

In step b) of the method of the present invention, the mixing time is not specifically limited, but is generally 2-10 minutes, and preferably 3-5 minutes, depending on the composition of the mixture. If the mixing time is excessively long, the flowability of the mixture can be reduced. Thus, the mixing time is determined according to the composition of the mixture.

The prepared mixture may be dry-compressed into a tablet directly, and in this case, the natural lubricant functions to prevent sticking of the mixture and impart a lubricant property to the mixture, but does not function to improve the flowability of the mixture. Accordingly, the flowability of the mixed powder is not ensured, and thus the mixed powder cannot flow out from the hopper of a tablet compression machine and cannot be uniformly filled into the bottom of the tablet compression machine. For this reason, a dry granulation process which uses a roller compactor is preferably carried out.

The roller compactor is widely used as one of dry granulation processes which are generally used. In the roller compactor, the pharmacological mixture is passed between rotating rollers, and it is compacted to form a compact or a sheet, which is then ground to a suitable size to form granules, which are then compressed into a tablet.

In the case in which the dry granulation process of compacting the mixed powder using the roller compactor to form a sheet and granulating the sheet is carried out, the flowability of the mixed powder can be ensured. It is noteworthy that the natural lubricant functions to prevent the mixed powder from sticking to the roller of the compactor and that the lubricant ability thereof is significantly reduced after the compaction process. For this reason, an additional amount of the natural lubricant is preferably added to and mixed with the mixed powder before tablet compression.

The natural lubricant that is added to and mixed with the mixed powder after the compaction process may be present in an amount of about 0.1-10 wt %, and preferably 2-4 wt %, based on the total weight of the natural tablet.

Mode For Invention

Hereinafter, the present invention will be described in detail with reference to examples. It is to be understood, however, that these examples are for illustrative purposes only and are not intended to limit the scope of the present invention.

EXAMPLES

Preparation of Tablet

The preparation of the natural tablet according to the present invention was based on mixing an active ingredient and an excipient (binder or disintegrant) to form a first mixture and then adding white bean powder (crude fat content: 16±4%) as a natural lubricant to the first mixture to form a second mixture, followed by direct compression.

If necessary, the mixture was subjected to a compaction process using a roller compactor in order to improve the flowability of the mixture, and then granulated, and the granules were compressed into a tablet using a rotary tablet compression machine.

Compaction molding conditions in the roller compactor are as follows:
Compaction molding conditions
Vector roller compactor TF 156
Roll speed: 8 rpm
Feed screw speed: 30 rpm Example 1

47 wt % of mixed plants extract powder and 53 wt % of seaweed calcium powder were mixed with each other, and the mixed powder was uniformly mixed in a double cone mixer for 30 minutes. Then, the mixture was compressed into tablets with a total weight of 800±50 mg and an average hardness of 10±3 kg using a rotary tablet compression machine.

Example 2

White bean powder (crude fat content: 16±4%) was added to and mixed with the mixed powder of Example 1 for 5 minutes in an amount of 3 wt % based on the total weight of the mixture. Then, the mixture was compressed into tablets with a total weight of 800±50 mg and an average hardness of 10±3 kg using a rotary tablet compression machine.

Example 3

White bean powder (crude fat content: 16±4%) was added to and mixed with the mixed powder of Example 1 for 5 minutes in an amount of 6 wt % based on the total weight of the mixture. Then, the mixture was compressed into tablets with a total weight of 800±50 mg and an average hardness of 10±3 kg using a rotary tablet compression machine.

Example 4

White bean powder (crude fat content: 16±4%) was added to and mixed with the mixed powder of Example 1 for 5 minutes in an amount of 3 wt % based on the total weight of the mixture. The resulting mixture was compacted using a roller compactor, and then granulated, and the granules were compressed into tablets with a total weight of 800±50 mg and an average hardness of 10±3 kg using a rotary tablet compression machine.

Example 5

White bean powder (crude fat content: 16±4%) was added to and mixed with the mixed powder of Example 1 for 5 minutes in an amount of 3 wt % based on the total weight of the mixture. The resulting mixture was compacted using a roller compactor, and then granulated. Then, white bean powder (crude fat content: 16±4%) was added to and mixed with the granules in an amount of 3 wt % based on the total weight of the granules. Then, the mixture was compressed into tablets with a total weight of 800±50 mg and an average hardness of 10±3 kg using a rotary tablet compression machine.

Comparative Example 1

Magnesium stearate was added to and mixed with the mixed powder of Example 1 for 5 minutes in an amount of 1 wt % based on the total weight of the mixture. Then, the mixture was compressed into tablets with a total weight of 800±?50 mg and an average hardness of 10±3 kg using a rotary tablet compression machine.

Test Example 1

Evaluation of Lubricant Properties

In order to examine the degree of improvement in lubricant properties, which is caused by the use of the natural lubricant according to the present invention, sticking during the tablet compression process in Examples 1 to 6 and Comparative Example 1 was observed and measured. Example 1 was used as a control. The lubricant property during the tablet compression process in the Examples was evaluated on the following scale: (−) poor; (+) moderate; (++) good; and (+++) excellent. In addition, the flowability was evaluated on the same scale as above.

Criteria for evaluating the lubricant property were based on the time point that the occurrence of sticking is shown during the tablet compression with the high-speed rotary tablet compression machine.

Specifically, the lubricant property was evaluated on the following scale: 10 or less tablets: poor; 10-50 tablets: moderate; 50-500 tablets: good; and 500 or more tablets: excellent. Criteria for evaluating the flowability of the mixture are associated with the degree to which the mixture is filled in the hopper of the tablet compression machine. Specifically, the flowability was evaluated based on the variation in the weight of tablets on the following scale: excellent: the variation in the total weight of 20 tablets is 5 wt % or less; good: 5-8 wt %; moderate: 8-12 wt %; and poor: 12 wt % or more.

The results of the evaluation are shown in Table 1 below.

TABLE 1

| Example | Lubricant property (evaluation of sticking) | Flowability |
|---|---|---|
| Example 5 | +++ | +++ |
| Example 4 | + | +++ |
| Example 3 | +++ | − |
| Example 2 | ++ | + |
| Example 1 | − | + |
| Comparative Example 1 | +++ | ++ |

As can be seen in Table 1 above, the lubricant property in Example 3 in which the white bean powder (crude fat content: 16±4%) was used in an amount of 6 wt % based on the total weight of the mixture was excellent compared to that in Example 2 in which the white bean powder was used in an amount of 3 wt %, but the flowability in Example 3 was significantly reduced compared to that in Example 2. Thus, it could be seen that the white bean powder should be used in an amount of 1-10 wt %, and preferably 2-4 wt %, in order to ensure the flowability of the mixture.

When Examples 2 and 4 were compared, it was shown that the flowability was ensured by the roller compaction process, but the lubricant property was slightly reduced. Based on these results, it can be seen that the white bean powder was additionally added to the mixture as described in Example 5 in order to increase the lubricant property of the mixture.

Accordingly, it could be seen that the use of the crude fat-containing bean powder as a natural lubricant according to the present invention can provide an effect equal to or higher than that obtained by the use of a conventional synthetic lubricant.

The invention claimed is:

1. A tablet comprising an active ingredient and a bean powder, wherein said bean powder is suitable for use as a natural lubricant in a tablet.

2. The tablet of claim 1, wherein the tablet a solid pharmaceutical or food formulation.

3. A method for preparing a natural tablet, the method comprising the steps of:
   a) mixing an active ingredient, a binder, an excipient and a disintegrant to prepare mixed powder;
   b) adding to and mixing with the mixed powder the natural lubricant of claim 1; and
   c) compacting the mixed powder using a roller compactor so as to form a sheet and granulating the sheet.

4. The method of claim 3, wherein the binder is a natural calcium material selected from the group consisting of seaweed calcium powder, shell calcium powder, and egg-shell calcium powder.

5. The method of claim 3, wherein the binder is added in an amount of 0-60 wt % based on the total weight of the natural tablet.

6. The method of claim 3, wherein the natural lubricant is added in an amount of 0.1-10 wt % based on the total weight of the natural tablet.

7. The method of claim 3, wherein the method further comprises, after granulating the sheet in step (c), a step of additionally adding the natural lubricant to the granules and compressing the mixture directly into a tablet.

8. The method of claim 7, wherein the natural lubricant is additionally added in an amount of 0.1-10 wt % based on the natural tablet.

* * * * *